US010557846B2

(12) United States Patent
Kwon et al.

(10) Patent No.: US 10,557,846 B2
(45) Date of Patent: Feb. 11, 2020

(54) ENCODED POLYMERIC MICROPARTICLES (71) Applicant: SNU R&DB FOUNDATION, Seoul (KR)

(72) Inventors: Sunghoon Kwon, Seoul (KR); Mira Kim, Seoul (KR); Jisung Jang, Seoul (KR); Hyungjong Bae, Seoul (KR); Nari Kim, Seoul (KR)

(73) Assignee: QUANTAMATRIX INC., Seoul (KR)

( * ) Notice: Subject to any disclaimer, the term of this patent is extended or adjusted under 35 U.S.C. 154(b) by 945 days.

(21) Appl. No.: 14/129,546

(22) PCT Filed: Nov. 18, 2013

(86) PCT No.: PCT/KR2013/010457
§ 371 (c)(1),
(2) Date: Dec. 27, 2013

(87) PCT Pub. No.: WO2014/077645
PCT Pub. Date: May 22, 2014

(65) Prior Publication Data
US 2014/0228252 A1    Aug. 14, 2014

(30) Foreign Application Priority Data

Nov. 16, 2012  (KR) ........................ 10-2012-0130096

(51) Int. Cl.
G01N 33/543 (2006.01)
C12Q 1/68 (2018.01)
C12Q 1/6825 (2018.01)
C12Q 1/70 (2006.01)
G01N 33/531 (2006.01)

(52) U.S. Cl.
CPC ....... *G01N 33/5434* (2013.01); *C12Q 1/6825* (2013.01); *C12Q 1/708* (2013.01); *G01N 33/531* (2013.01)

(58) Field of Classification Search
None
See application file for complete search history.

(56) References Cited

U.S. PATENT DOCUMENTS

| 7,709,544 | B2 | 5/2010 | Doyle et al. | |
|---|---|---|---|---|
| 2004/0101822 | A1 | 5/2004 | Wiesner et al. | |
| 2006/0105170 | A1* | 5/2006 | Dobson | B82Y 25/00 428/403 |
| 2010/0048416 | A1 | 2/2010 | Wilson | |
| 2011/0108523 | A1* | 5/2011 | Yang | C08J 9/26 216/56 |
| 2011/0226990 | A1* | 9/2011 | Glennon | B01J 20/283 252/184 |
| 2012/0028834 | A1* | 2/2012 | Kwon | B82Y 25/00 506/9 |
| 2012/0295297 | A1 | 11/2012 | Kwon et al. | |
| 2012/0326104 | A1* | 12/2012 | Kwon | B82Y 20/00 252/583 |

FOREIGN PATENT DOCUMENTS

| CN | 1775654 | A | | 5/2006 |
|---|---|---|---|---|
| CN | 101912757 | A | | 12/2010 |
| CN | 102120168 | A | | 7/2011 |
| JP | 2006517985 | | | 8/2006 |
| KR | 10-2005-0109455 | A | | 11/2005 |
| KR | 10-1101310 | B1 | | 12/2011 |
| WO | WO1996011054 | | * | 4/1996 |
| WO | WO2001088540 | | * | 11/2001 |
| WO | 2008/084243 | A1 | | 7/2008 |
| WO | 2008/084247 | A1 | | 7/2008 |

OTHER PUBLICATIONS

Lee et al.( Nature materials 9.9 (2010): 745-749.).*
Tissot et al. (Macromolecules 34.17 (2001): 5737-5739.).*
Bae, Hyung Jong, et al. (Proceedings of 16th International Conference on Miniaturized Systems for Chemistry and Life Sciences, Oct. 28-Nov. 1, 2012). (Year: 2012).*
Kim et al. ( Angewandte Chemie International Edition 50.5 (2011): 1171-1174; published online Dec. 22, 2010.) (Year: 2010).*
Tian et al.( Chem. Mater. 2010, 22, 2069-2078). (Year: 2010).*
Chung et al. ( Applied Physics Letters 91.4 (2007): 041106.). (Year: 2007).*
Zhang et al.,"Synthesis of Silanol-Functionalized Latex Nanoparticles tMiniemulsion Copolymerization of Styrene and y-Methacryloxypropyltrimethoxysilane", Langmuir 2006, 22, 4674-4679.
Shin-Hyun Kim al.,"Microfluidic Multicolor Encoding of Microspheres with Nanoscopic Surface Complexity for Multiplex Immunoassays", Angew. Chem. 2011, 123, 1203-1206.
Bo He et al, Suspension Array with Shape-Coded Silica Nanotubes for Multiplexed Immunoassays, Anal. Chem. 2007, 79, 5257-5263.
Petra Haufová et al, Reversible buckling and diffusion properties of silica-coated hydrogel particles, Journal of Colloid and Interface Science 357 (2011) 109-115.
Jason E. Meiring et al, Hydrogel Biosensor Array Platform Indexed by Shape, Chem. Mater. 2004, 16, 5574-5580.

(Continued)

*Primary Examiner* — Tracy Vivlemore
*Assistant Examiner* — Sahana S Kaup
(74) *Attorney, Agent, or Firm* — STIP Law Group, LLC (57) ABSTRACT Provided are encoded polymeric microparticles and a multiplexed bioassay using the encoded polymeric microparticles. Each of the encoded polymeric microparticles includes an encoded polymeric microparticle core and a silica shell surrounding the microparticle core. Further provided is a method for producing encoded polymeric microparticles. The method includes: mixing a photocurable material with a linker having a functional group polymerizable with the photocurable material and an alkoxysilyl group; applying patterned energy to cure the mixture, followed by encoding to obtain encoded polymeric microparticle cores; and treating the encoded polymeric microparticle cores with a silica precursor to form a silica shell on each encoded polymeric microparticle core.

8 Claims, 9 Drawing Sheets

(56) References Cited

OTHER PUBLICATIONS

Saemi Park et al, Multiplex Immunoassay Platforms Based on Shape-Coded Poly(ethylene glycol) Hydrogel Microparticles Incorporating Acrylic Acid, Sensors 2012, 12, 8426-8436; doi:10.3390/s120608426.
Kevin Braeckmans et al, Encoding Microcarriers: Present and Future Technologies, Nature Reviews Drug Discovery, vol. 1, Jun. 2002, pp. 447-456.
Japanese Office Action with English translation.
Y.-c. Cao et al., "Preparation of silica encapsulated quantum dot encoded beads for multiplex assay and its properties", Quantum dot encoded beads for multiplex assay, Anal. Biochem. 351 (2006) 193-200.
B.-H. Jun et al.,"Protein separation and identification using magnetic beads encoded with surface-enhanced Raman spectroscopy", Magnetic beads encoded with SERS, Anal. Biochem. 391 (2009) 24-30.
Jun et al., Surface-Enhanced Raman Spectroscopic-Encoded Beads for Multiplex Immunoassay, Journal of Combinatorial Chemistry, 2007, vol. 9, No. 2, 237-244.
European Search Report for European Patent Application No. 13855838.2 dated Feb. 1, 2016 from European Office Patent.

\* cited by examiner

(A) Polymer surface (B) Formation of silica particles on polymer surface (C) Coalescence of silica particles (D) Completion of silica shell

FIG. 5

Silica-coated polymer microparticle

ENCODED POLYMERIC MICROPARTICLES

CROSS REFERENCE TO PRIOR APPLICATIONS

This application is a National Stage Application of PCT International Patent Application No. PCT/KR2013/010457 filed on Nov. 18, 2013, under 35 U.S.C. § 371, which claims priority to Korean Patent Application Nos. 10-2012-0130096 filed on Nov. 16, 2012, which are all hereby incorporated by reference in their entirety.

FIELD OF THE DISCLOSURE

The present disclosure relates to encoded polymeric microparticles. More specifically, the present disclosure relates to encoded polymeric microparticles that have superior chemical and physical stability and can be produced on a large scale, a method for producing the encoded polymeric microparticles, and a multiplexed bioassay using the encoded polymeric microparticles.

BACKGROUND

Recently, encoded polymeric microparticles are widely used to detect bioanalytes (e.g., DNAs or proteins) owing to their simple fabrication processes and numerous coding capacities. However, encoded polymeric microparticles can be easily damaged due to poor physical/chemical durability of the constituent polymeric materials and can absorb analytes, causing analysis errors. Also, bioconjugations of polymeric microparticles with biomaterials are limited to a few special chemical processes and are not able to apply diverse conjugation chemistry. Thus, there is a need to develop microparticles that can be encoded, have superior chemical and physical stability, are functionalized with various functional groups, and can be produced on a large scale.

SUMMARY

One embodiment of the present disclosure provides encoded polymeric microparticles, each of which includes an encoded polymeric microparticle core and a silica shell surrounding the microparticle core.

A further embodiment of the present disclosure provides a method for producing encoded polymeric microparticles, the method including: mixing a photocurable material with a linker having a functional group polymerizable with the photocurable material and an alkoxysilyl group; applying patterned energy to cure the mixture, followed by encoding to obtain encoded polymeric microparticle cores; and treating the encoded polymeric microparticle cores with a silica precursor to form a silica shell on each encoded polymeric microparticle core.

Another embodiment of the present disclosure provides a multiplexed bioassay using encoded polymeric microparticles, each of which includes an encoded polymeric microparticle core, a silica shell surrounding the microparticle core, and a biomaterial bound to the silica shell.

BRIEF DESCRIPTION OF THE DRAWINGS

The above and other embodiments and advantages of the disclosure will become apparent and more readily appreciated from the following description of the embodiments, taken in conjunction with the accompanying drawings of which.

DETAILED DESCRIPTION

Embodiments of the present disclosure will now be described in more detail with reference to the accompanying drawings. These embodiments are provided so that this disclosure will fully convey the scope of the disclosure to those skilled in the art. Accordingly, the present disclosure may be embodied in many different forms and should not be construed as limited to the exemplary embodiments set forth herein. In the drawings, the dimensions, such as widths, lengths and thicknesses, of elements may be exaggerated for clarity. It will be understood that when an element is referred to as being "on" another element, it can be directly on the other element, or one or more intervening elements may also be present therebetween.

Figure 1:
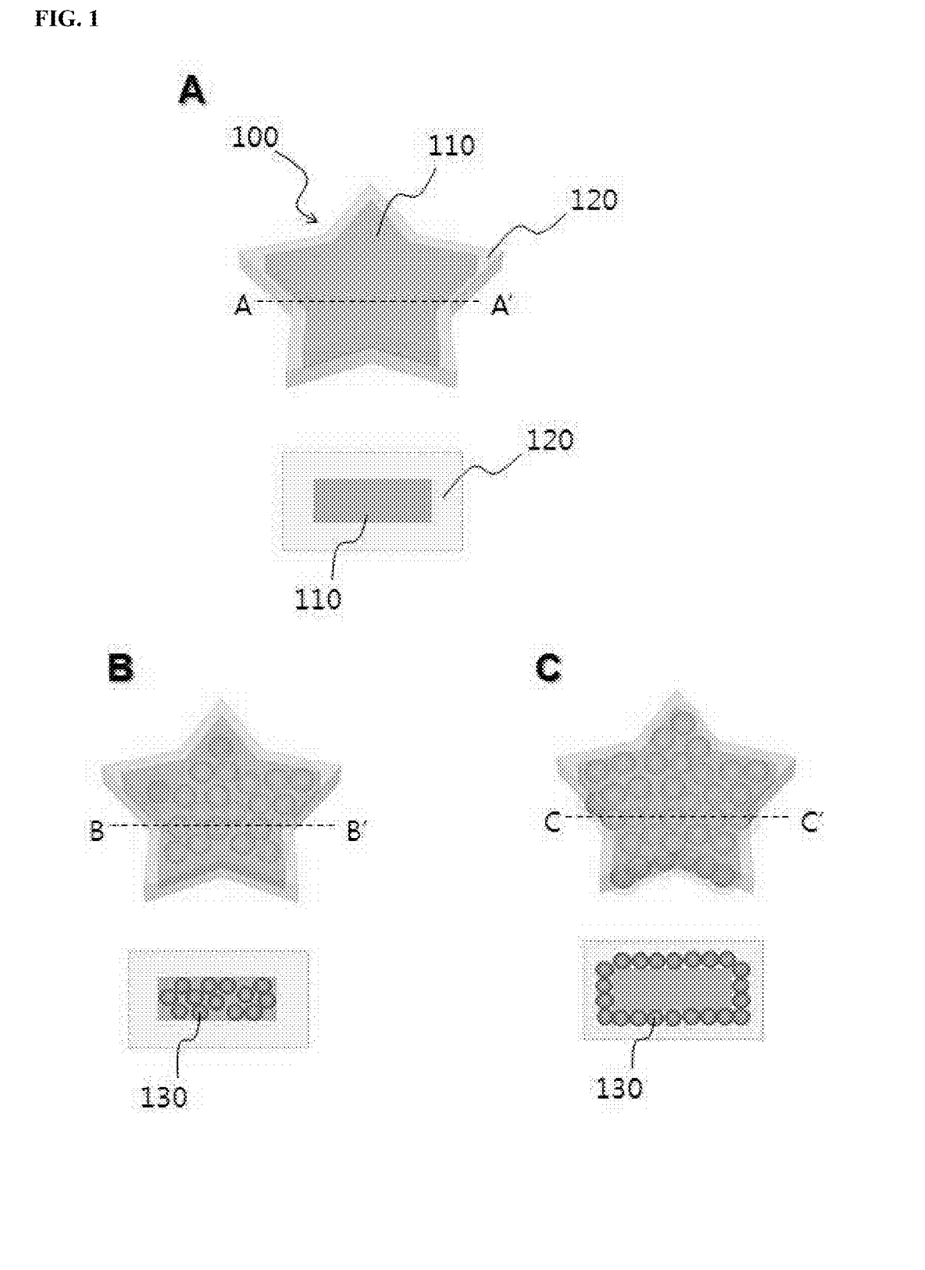
FIG. 1 shows encoded polymeric microparticles according to one embodiment of the present disclosure.

FIG. 1 shows encoded polymeric microparticles according to one embodiment of the present disclosure. In FIG. 1, the lower views of A, B, and C show cross sections taken along lines A-A', B-B', and C-C', respectively. Referring to A of FIG. 1, an encoded polymeric microparticle 100 includes an encoded polymeric microparticle core 110 and a silica shell 120 surrounding the microparticle core. The core 110 may be encoded by various processes known in the art. For example, the encoded polymeric microparticle core 110 may include a graphical, fluorescent or color code.

The polymeric microparticle core 110 is preferably composed of a photocurable polymer that can be variously patterned by optical lithography. The photocurable polymer may contain a curable acrylic material as a major component. Preferably, the photocurable polymer contains a linker material having a photocurable functional group capable of reacting with the photocurable material and a functional group capable of forming silica, in addition to the photocurable acrylic material.

The polymeric microparticle core 110 made by photocuring may have various shapes such as disc-like and spherical shapes. The core 110 may have a size in the range of several micrometers to several millimeters.

The encoded polymeric microparticle 100 may further include magnetic materials. Specifically, the microparticle core 110 may further contain magnetic nanoparticles 130 therein (B of FIG. 1). Alternatively, a layer of magnetic nanoparticles 130 may be interposed between the microparticle core 110 and the silica shell 120 (C of FIG. 1). In this case, a strong magnetic field is required during subsequent control of the microparticle 100 due to a relatively small amount of the magnetic nanoparticles 130, but no influence is given to patterning by photocuring because no light scattering is caused by the magnetic nanoparticles 130, thus being advantageous in microstructure patterning compared to the former case. The presence of the magnetic nanoparticles in the encoded polymeric microparticle 100 enables control of the microparticle 100 by an external magnetic field. As a result, the microparticle 100 can be efficiently used for a solution exchange of a subsequent bioassay and the separation of the microparticle 100 is possible, leading to high accuracy and improved convenience of the bioassay.

The silica shell 120 surrounds and protects the microparticle core 110 and prevents absorption of external detection materials into the polymer of the microparticle core 110 causing analysis errors. The silica shell 120 imparts chemical and mechanical stability to the encoded polymeric microparticle 100 and helps to use the microparticle 100 in a wide variety of environments and solutions. The encoded polymeric microparticle core 110 can be connected to the silica shell 120 via —Si—O—Si— bonds. The strong chemical bonds between the core 110 and the shell 120 can ensure a stable structure of the microparticle 100. The presence of the silica shell 120 lowers the binding of unspecific materials to the surface of the polymeric microparticle 100 and ensures improved binding properties with biomaterials. Functional groups such as carboxyl or amine groups may be introduced on the surface of the silica shell 120. The functional groups can form covalent bonds with various biomolecules for diverse biomedical applications or clinical diagnostics. For example, a biomaterial selected from the group consisting of antigens, antibodies, DNAs, RNAs, and oligonucleotides may be introduced on the surface of the silica shell 120.

Figure 2:
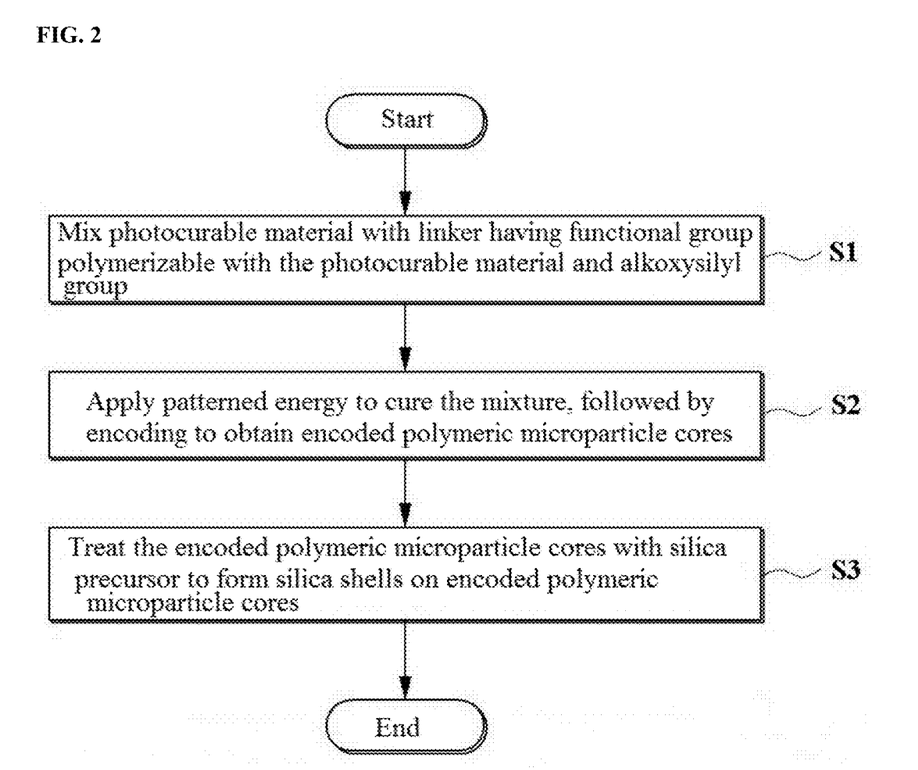
FIG. 2 is a flow chart showing a method for producing encoded polymeric microparticles.

The encoded polymeric microparticles according to the embodiment of the present disclosure can be produced by the following procedure. FIG. 2 is a flow chart showing a method for producing the encoded polymeric microparticles. Referring to FIG. 2, in step S1, a photocurable material is mixed with a linker having a functional group polymerizable with the photocurable material and an alkoxysilyl group.

The photocurable material is cured by subsequent energy application to make a basic skeleton of the microparticles. Examples of suitable photocurable materials include ethoxylated trimethylolpropane triacrylate, 2-hydroxyethyl methacrylate, methyl methacrylate, acrylamide, allyl amine, polyethylene oxide, polyethylene glycol diacrylate, polypropylene glycol diacrylate, polyvinylpyrrolidone, polyvinyl alcohol, and polyacrylate. These photocurable materials may be used alone or in combination thereof. For example, polyethylene glycol diacrylate as the photocurable material may be cross-linked into a three-dimensional hydrogel via free radical polymerization due to the presence of acrylate groups at both ends of polyethylene glycol. The photocurable material may be any material that can be changed from a liquid to a solid by external light.

The linker reacts with the photocurable material to form a copolymer as a skeleton of the microparticles, and at the same time, it allows alkoxysilyl groups to be grafted onto the surface of encoded microparticle cores. If the microparticles are composed of the photocurable material alone, silica shells are not easy to form through subsequent silica coating. In contrast, when the mixture of the photocurable material and the linker is cured to obtain microparticle cores in the subsequent step of the method according to the embodiment of the present disclosure, alkoxysilyl groups are grafted onto the surface of the microparticle cores, and thereafter, silica shells can be coated on the microparticle cores through the alkoxysilyl groups.

For example, the linker may be a compound represented by Formula 1:

(1)

wherein $R_1$ is hydrogen, methyl or ethyl, each $R_2$ is $C_1$-$C_8$ straight or branched alkyl, and L is $C_1$-$C_{12}$ alkylene, arylene or any combination thereof. Specifically, the linker of Formula 1 may be 3-(trimethoxysilyl)propyl acrylate (TMSPA).

The mixture may further include an initiator. The initiator may induce free radical polymerization of the mixture by an external energy source. The initiator may be an azo-based compound or a peroxide. The mixture may further include a proper cross-linking agent. Examples of such cross-linking agents include N,N'-methylenebisacrylamide, methylenebismethacrylamide, and ethylene glycol dimethacrylate.

If necessary, the method may further include adding magnetic nanoparticles to the mixture to control the encoded polymeric microparticles. As a result, the magnetic nanoparticles may be introduced into polymeric microparticle cores.

In step S2, patterned energy is applied to cure the mixture, followed by encoding to obtain encoded polymeric microparticle cores. The patterned energy is not limited and may be, for example, ultraviolet light, visible light, infrared light or electron beam. For example, ultraviolet light as the patterned energy may be irradiated through a physical mask or a digital micromirror device (DMD).

The encoding may be performed by various processes. In one embodiment, the microparticle cores may be encoded, for example, by performing an optical lithography process to pattern graphical codes. The graphical codes may have the shape (e.g., star or circle shape) of the microparticles and may be binary codes engraved on the microparticles. Encoding of the graphical codes may be performed by applying the photocurable polymer to the production of the particles and patterning the particles by an optical lithography process, as described above.

The microparticles may be patterned by various lithography processes known in the art, for example, optofluidic lithography, which is described in Korean Patent No. 1004769, and a combination of flow lithography and polymerization, which is described in U.S. Pat. No. 7,709,544. For example, the microparticle cores may be encoded by patterning labels representing '1' and '0' on the photocurable polymer. The labels are distinguished from each other depending on the degree of photocuring. For example, a digital micromirror device using no mask may be employed for optical lithography. In this case, various kinds of codes, for example, as many as one million kinds of codes, can be advantageously formed on the particles including the target substance.

In a further embodiment, the encoding of the microparticle cores may be achieved by incorporating fluorescent materials with various colors distinguishable from each other into the microparticle cores. Various known techniques may be applied to incorporate fluorescent materials into the microparticle cores.

In another embodiment, a magnetic ink may be used to form color codes on the microparticle cores. For example, a method for forming color codes using a magnetic ink is disclosed in Korean Patent Application No. 10-2010-0029613. According to this method, an external magnetic field is applied to a photocurable material including magnetic nanoparticles to align the magnetic nanoparticles in the photocurable material, and external light is applied to cure the photocurable material. In response to the intensity of the external magnetic field, the array of the magnetic nanoparticles is varied to emit different colors. By the application of such techniques, magnetic nanoparticles can be arranged so as to be distinguished from each other in the microparticle cores composed of the photocurable polymer, so that color codes can be formed on the microparticle cores. The disclosure of the patent publication is incorporated herein by reference.

In one embodiment, the method may further include attaching magnetic nanoparticles coated with a hydrophilic polymer to the encoded polymeric microparticle cores to control the encoded polymeric microparticles.

Next, in step S3, the encoded polymeric microparticle cores are treated with a silica precursor to form a silica shell on each encoded polymeric microparticle core, completing production of the encoded polymeric microparticles. The silica shell formation may be performed by various processes known in the art, for example, via a modified Stober method.

First, the alkoxysilyl group-grafted microparticles are added to a solution of distilled water, ethanol, and $NH_4OH$. Next, tetraethylorthosilicate (TEOS) as a silica precursor is injected into the solution to react with the alkoxysilyl groups grafted onto the surface of the microparticle cores. As a result of the reaction, silica shells are formed and —Si—O—Si— bonds are formed at the core-shell interfaces.

Polymeric microparticles are flexible, soft and easy to fabricate various structures and shapes, but they also can be easily damaged, either mechanically or chemically. Also, small molecules can be absorbed into the polymer matrix causing detection errors. In contrast, inorganic materials, such as silica or titania, are typically much harder than organic polymers and have a good chemical stability, but are also brittle and difficult to produce various structures. Therefore, coating silica cells on polymeric microstructures could yield a combination of their beneficial properties, resulting in hard, tough, chemically stable and durable microparticles which are still easy to produce various shapes.

The silica-coated encoded polymeric microparticles can be applied to multiplexed bioassays. In current approaches for multiplexed bioassays, encoded polymeric microparticles are used to analyze biomolecules such as DNAs or proteins. These approaches are very powerful and versatile, since they allow for nearly unlimited codes and high-throughput analysis. In one embodiment of the present disclosure, the surface of the silica shells may be modified to introduce carboxyl or amine groups thereon. This surface modification enables application of the encoded polymeric microparticles to multiplexed bioassays. Such functional groups can form covalent bonds with various biomaterials. The method may further include binding biomaterials to the surface of the silica shells.

Figure 3:
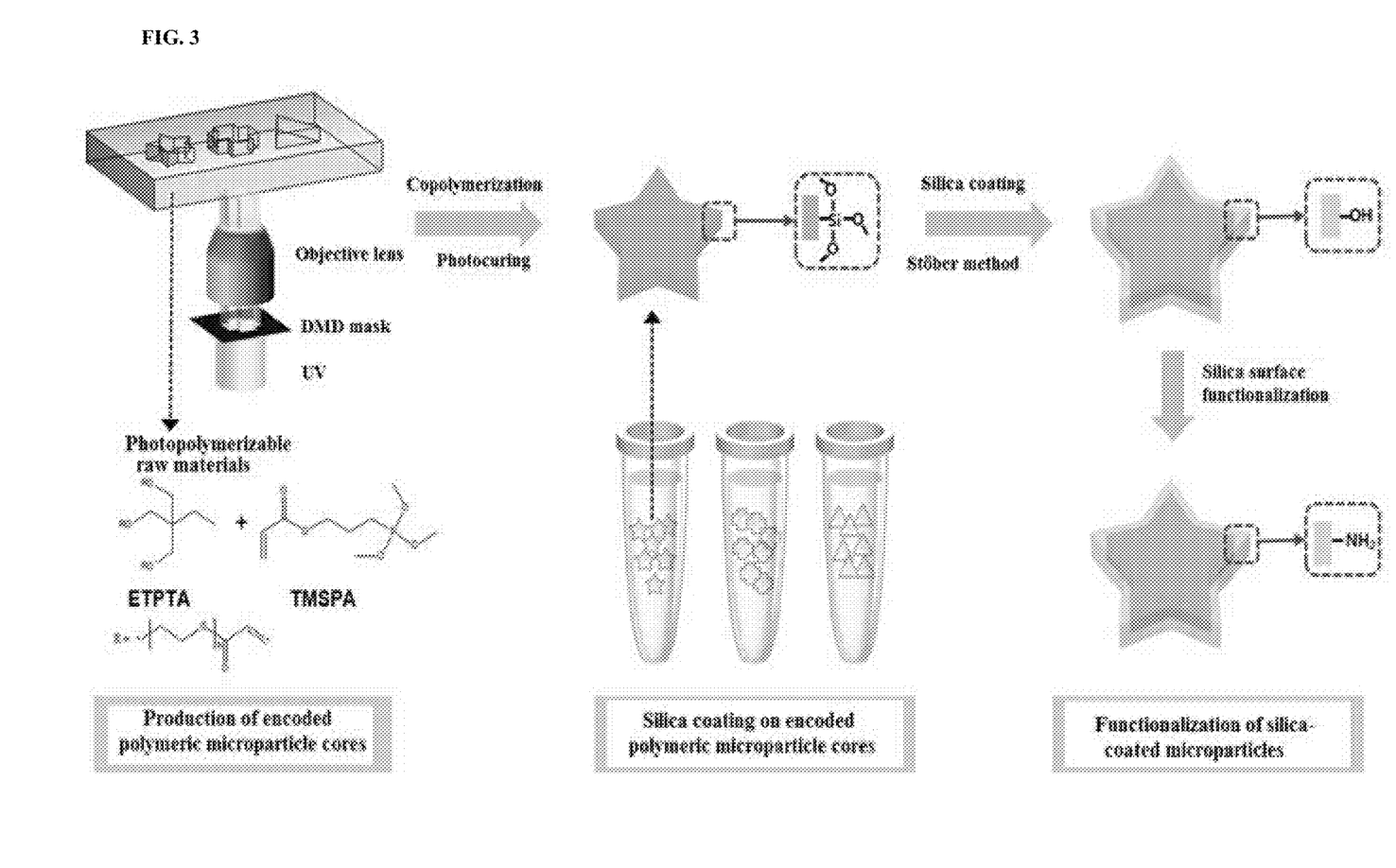
FIG. 3 shows a procedure for producing encoded polymeric microparticles according to one embodiment of the present disclosure.

FIG. 3 shows a procedure for producing encoded polymeric microparticles according to one embodiment of the present disclosure. Referring to FIG. 3, polymeric microparticles having graphical codes are fabricated by the following procedure. First, ethoxylated trimethylopropane triacrylate (ETPTA) as a photocurable material, 3-(trimethoxysilyl) propyl acrylate (TMSPA) as a linker, and 2-hydroxy-2-methylpropiophenone as a photoinitiator are mixed in an appropriate ratio of 10:1:1 to prepare a photocurable mixture. The acrylate group of TMSPA can participate in the photocuring reaction of the acrylate matrix. In addition, TMSPA serves as a seed for subsequent silica coating because it has a silicon-centered silane group that can form silica. Patterned UV light may be irradiated onto the mixture by various lithography processes known in the art, including optofluidic maskless lithography shown in FIG. 3, to make alkoxysilane-containing copolymer microparticles having graphical codes. According to optofluidic maskless lithography (OFML), the raw materials are introduced through microfluidic channels and patterned energy is applied to induce in-situ photopolymerization of the raw materials. As a result of the photopolymerization, free-floating particles can be continuously produced. In addition, the maskless process using a digital micromirror device (DMD) enables the production of encoded particles with various shapes in a simple manner, compared to other lithography processes using masks.

Silica coating on the copolymer microparticles is carried out through a modified Stober method to form silica shells. This simple coating process is very fast, allowing direct and efficient silica coating on silane group-containing microparticles. In addition, the process enables millions of silica-coated microparticles to be produced in a single step. The thickness of the silica shells can be controlled from several hundred nanometers to several micrometers by varying the reaction rate or the concentration of the silica precursor. The resulting silica shells of the microparticles can be functionalized with different functional groups via well-established silica surface chemistry.

Figure 4:
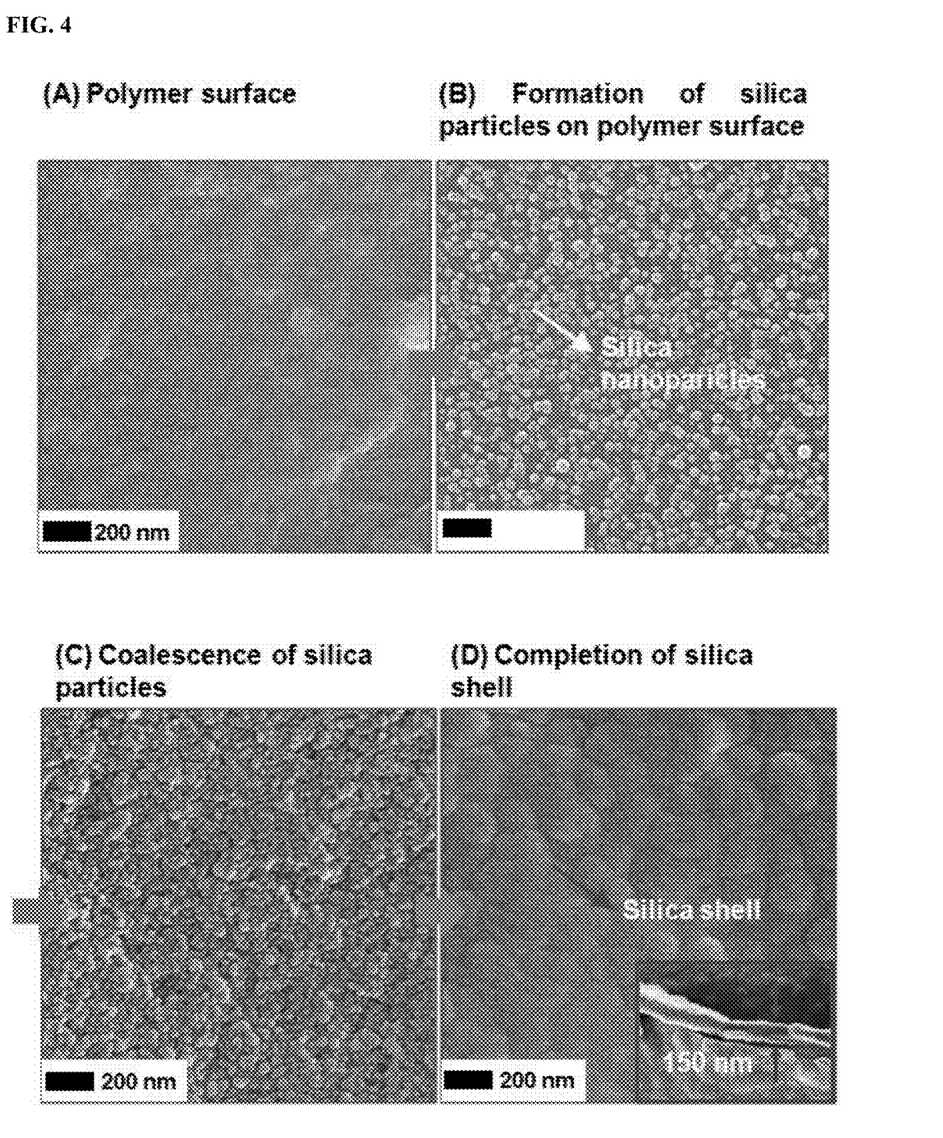
FIG. 4 shows scanning electron microscopy (SEM) images showing silica shell growth on the surface of a copolymer microparticle.

FIG. 4 shows scanning electron microscopy (SEM) images showing silica shell growth on the surface of the copolymer microparticle. Referring to FIG. 4, the coverage of silica varies depending on the degree of coating. Initially, the seed silica nanoparticles are formed on the surface of the copolymer microparticle. Then the seed nanoparticles begin to coalesce, until the complete formation of a continuous silica shell on the copolymer surface can be observed. The complete silica shell is shown in (D) of FIG. 4. The inset shows that the thickness of the silica layer is about 150 nm.

Figure 5:
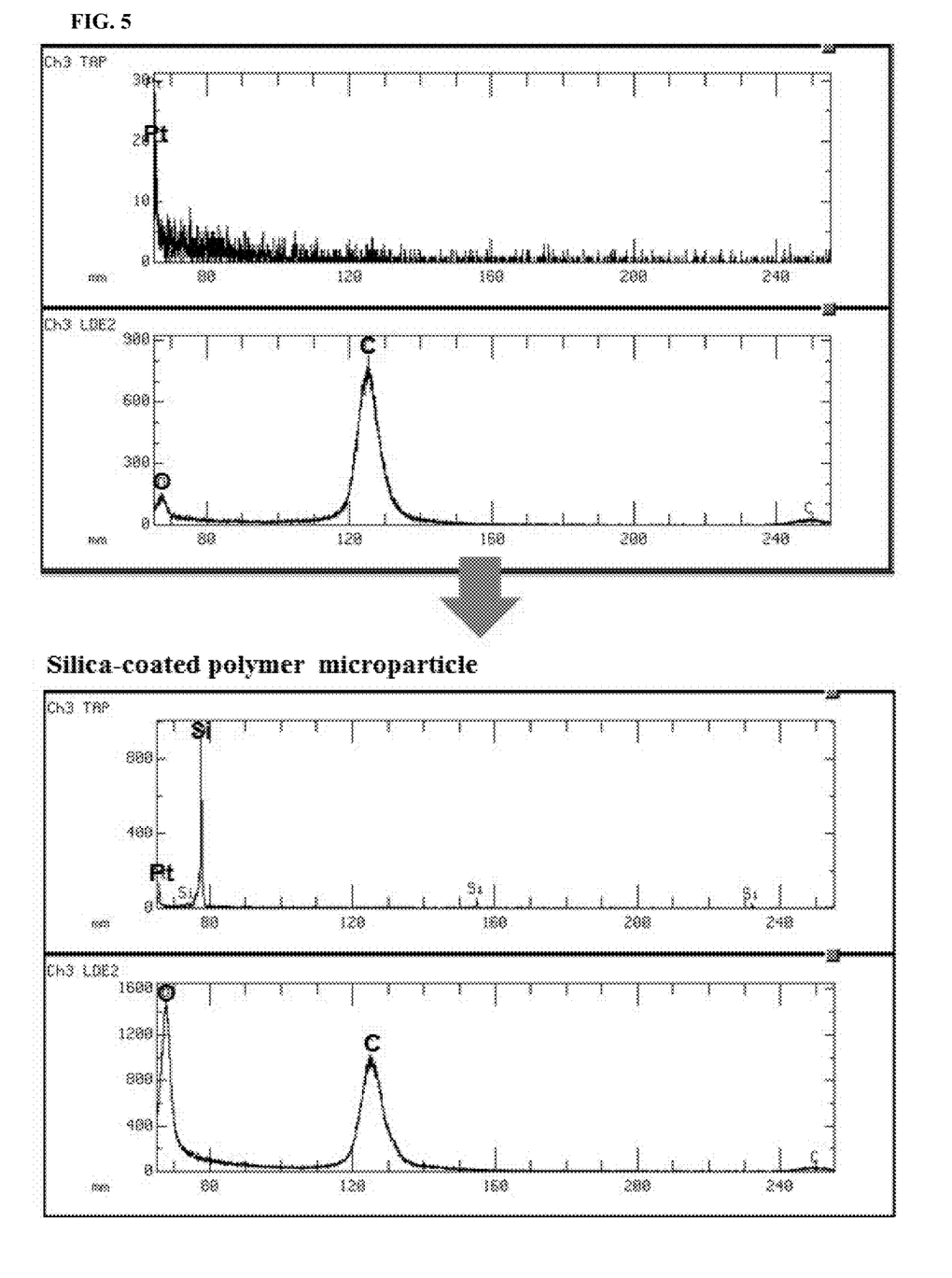
FIG. 5 shows electron probe microanalysis (EPMA) spectra of a silica-coated microparticle and an uncoated microparticle.

FIG. 5 shows electron probe microanalysis (EPMA) spectra of a silica-coated microparticle and an uncoated microparticle. Referring to FIG. 5, the uncoated polymeric microparticle was generated using ETPTA and a photoinitiator without TMSPA as a seed material. In the EPMA spectrum of the uncoated microparticle, strong C and weak O peaks were detected, indicating the presence of a bare organic polymer. Pt peak was detected because particles were coated with Pt by a sputter. It was confirmed that the pure silica shell is created on the polymeric microparticle as shown in the bottom spectra of FIG. 5. Three peaks were detected, those of Si, O and C, the signal of O being much stronger than that of C as expected from the presence of silica ($SiO_2$). The beam penetration depth of EPMA was 1 μm. Therefore, the signal of C was detected, since the thickness of the silica shell was below 1 μm.

Figure 6:
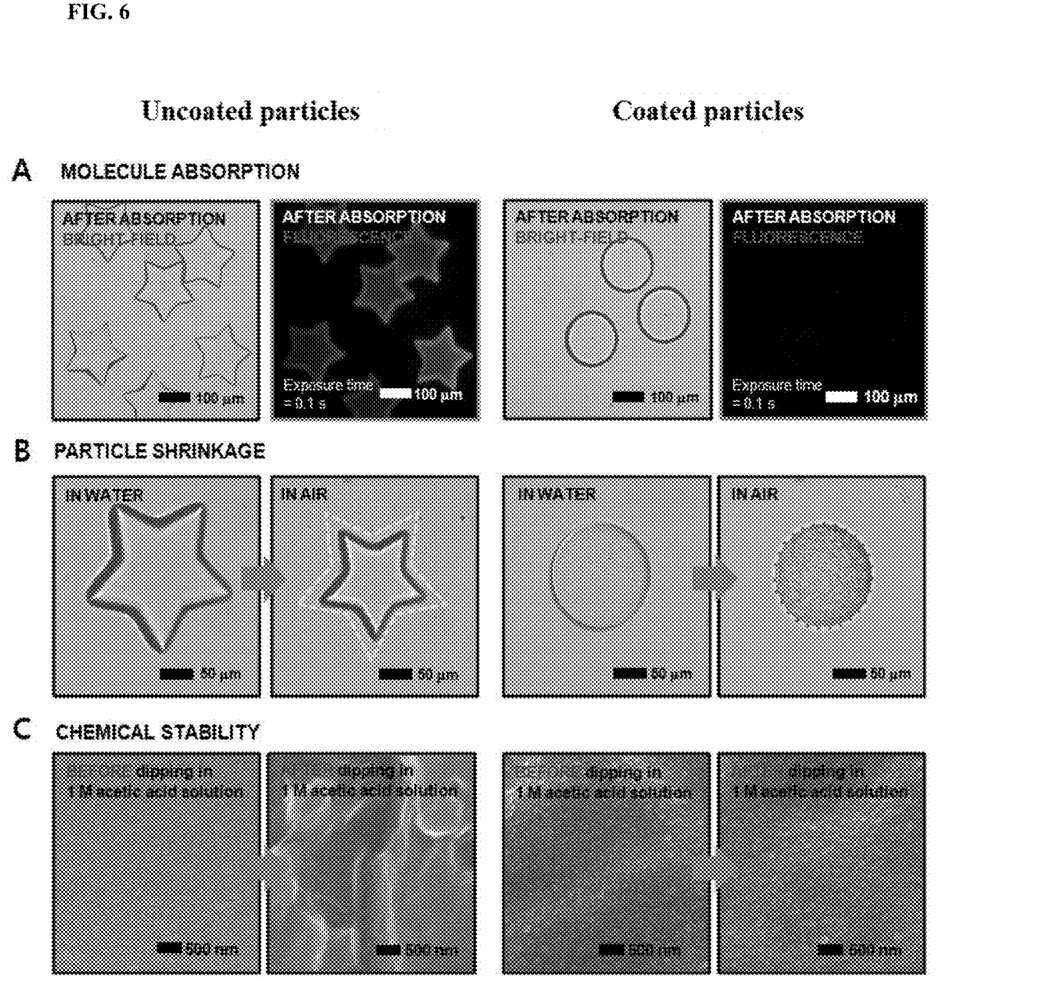
FIG. 6 shows images of star-shaped polymeric microparticles including no silica shells and circle-shaped polymeric microparticles including silica shells.

FIG. 6 shows images of star-shaped polymeric microparticles including no silica shells and circle-shaped polymeric microparticles including silica shells.

0.1 M rhodamine B aqueous solution (red fluorescence) was used to test chemical resistance of the silica-coated particles. FIG. 6A shows the absorption of the dye molecules into uncoated (star-shaped) and silica-coated (star-shaped) polymeric microparticles. As clearly shown in the fluorescent images, the rhodamine aqueous solution was well absorbed into the microparticle-constituting polymer hydrogel. It is well known that polymer hydrogels easily absorb liquid solutions without any chemical or physical treatments. However, the silica shell formed on the surface of the circle-shaped microparticle inhibits the absorption of the rhodamine aqueous solution into the polymer hydrogel. Therefore, the use of the silica-coated microparticles for bioassays can provide reliable and accurate results, since the absorption of biomaterials such as antigens or oligonucleotides causing analysis errors into the polymer matrix can be prevented. The absence of fluorescent signals from the images of the coated particles also shows that there is no detectable absorption of the dye on the silica surface, due to the low non-specific binding ability of silica.

Also the swelling or shrinkage behaviors of the silica-coated and uncoated microparticles were examined by placing the particles in water and in air. In general, polymeric hydrogels swell in water, since they absorb large quantities of water. After evaporation of water, the uncoated microparticles considerably shrunk, while the silica-coated microparticles remained their structure and volume under the dry condition, as shown in B of FIG. 6.

In order to investigate chemical stability of the silica-coated and uncoated microparticles, the microparticles were dipped in a 1 M acetic acid aqueous solution with agitation. After 24 hours, the silica-coated particles remained stable, while the uncoated particles were severely damaged in the acid solution as shown in C of FIG. 6. In general, polymer hydrogels are sensitive to external parameters such as pH and temperature. In contrast, silica materials are typically much harder than organic polymers and have a good chemical stability. Therefore, this robust silica-coated microparticle is less limited to introduction of functional groups since it can endure various chemical reactions even in organic solvents or under a dry condition.

The surface functionalization of the silica-coated polymeric microparticle provides specific functional groups which can be covalently attached to biomaterials with high stability and a low non-specific binding property.

Figure 7:
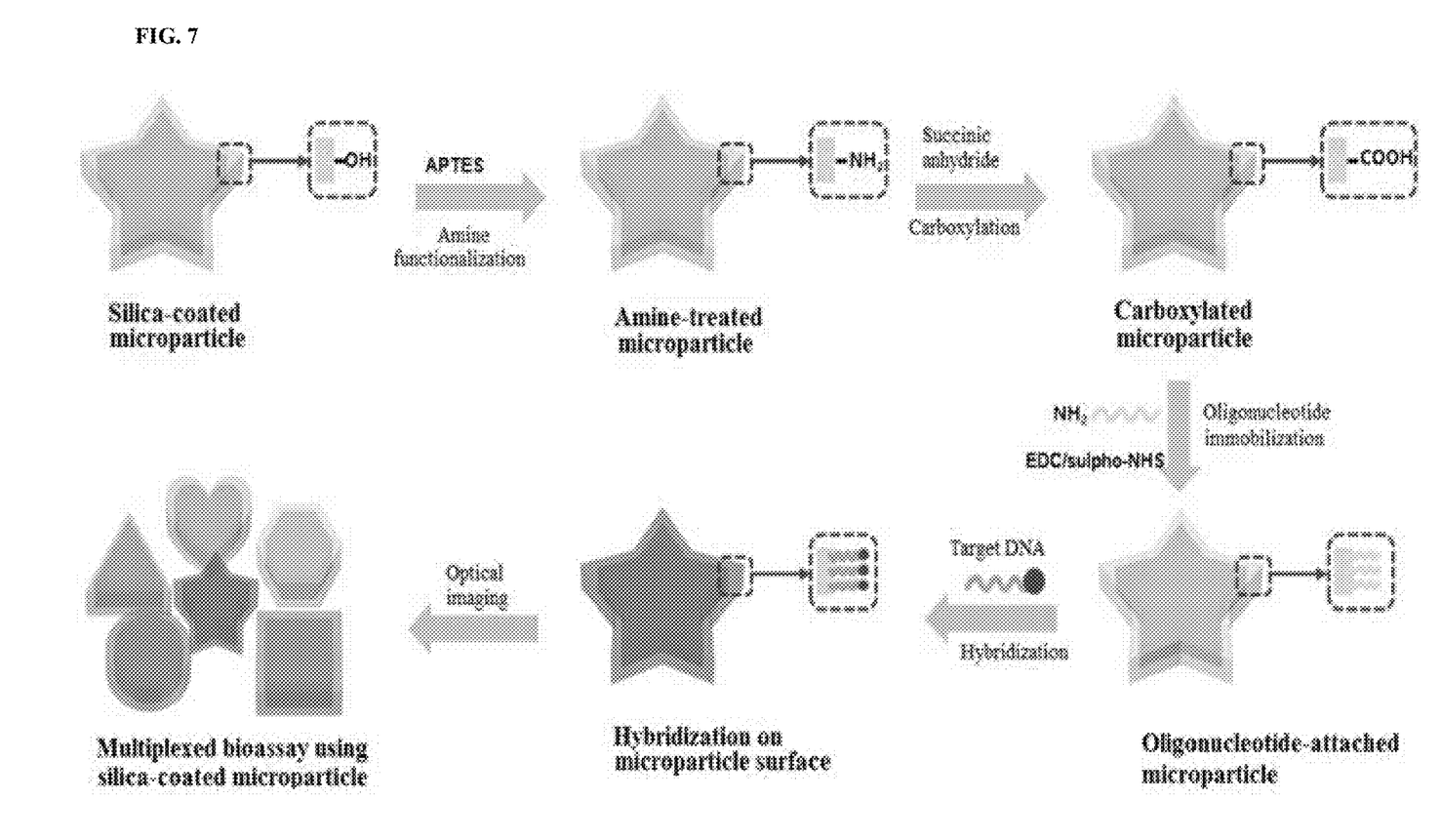
FIG. 7 shows a multiplexed DNA hybridization assay using oligonucleotides immobilized on the surface of a silica-coated polymeric microparticle.

FIG. 7 shows a multiplexed DNA hybridization assay using oligonucleotides immobilized on the surface of the silica-coated polymeric microparticle. Referring to FIG. 7, the silica-coated microparticle reacts easily with primary amines using 3-aminopropyltriethoxysilane (APTES) through condensation of terminal hydroxyl groups. The amines are subsequently reacted with succinic acid, resulting in a carboxylated surface able to react with amino groups on DNAs. 5' amino-terminated DNAs are used to immobilize DNAs on the carboxylated silica surface. An amide bond between the carboxylic group of the silica surface and an amino group of an amino-terminated DNA is formed by a cross-linking process using 1-ethyl-3-(3-dimethylaminopropyl)carbodiimide (EDC) and N-hydroxysulfosuccinicimide (sulfo-NHS).

Figure 8:
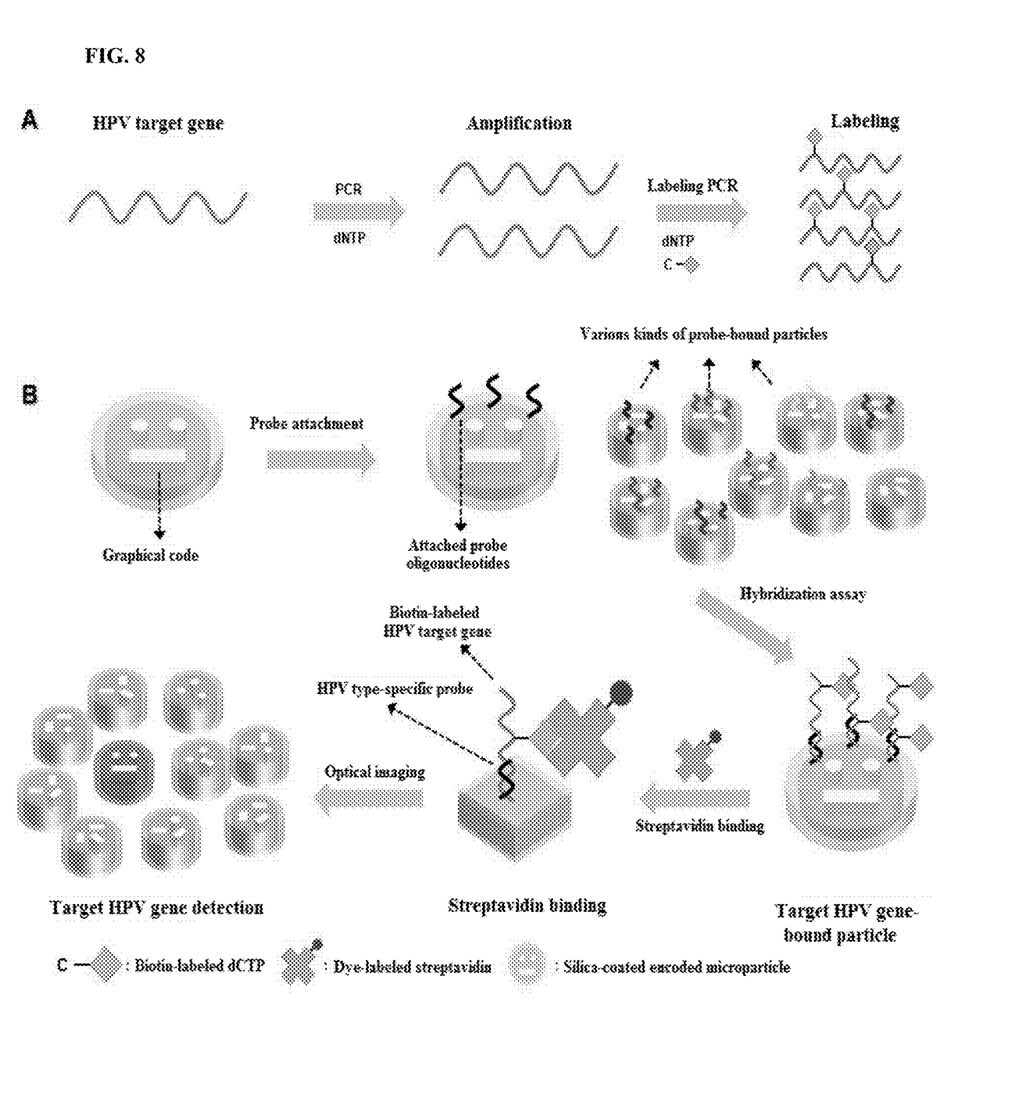
FIG. 8 shows a multiplexed HPV genotyping using silica-coated encoded polymeric microparticles.

The encoded polymeric microparticles according to the embodiment of the present disclosure offer useful benefits for multiplexed bioassays. To clarify the advantages of the microparticles, a 10-plex in vitro human papillomavirus (HPV) genotyping using the silica-coated microparticles was demonstrated. Target HPV genes were prepared with the 2-step PCR process. FIG. 8 shows a multiplexed HPV genotyping using the silica-coated encoded polymeric microparticles. FIG. 8A schematically shows amplification and labeling PCR. After amplification PCR, labeling PCR is performed to label probe-complementary HPV gene sequences using biotin-attached dCTP. FIG. 8B schematically shows 10-plexed HPV genotyping using probe-attached microparticles. 10 types of HPV type-specific oligonucleotide probes are coupled to silica surface of microparticles. Each of target HPV genes is complementary to one of the different probes. The graphical codes which are unpolymerized holes in the microparticle structures indicate the identity of probe types on the silica surface of microparticles. Multiplexing capacity of the particles could readily be augmented by modifying the graphical codes. After the hybridization assay with the target HPV sequence, fluorescent dye-labeled streptavidins are introduced to gain fluorescent signals.

Figure 9:
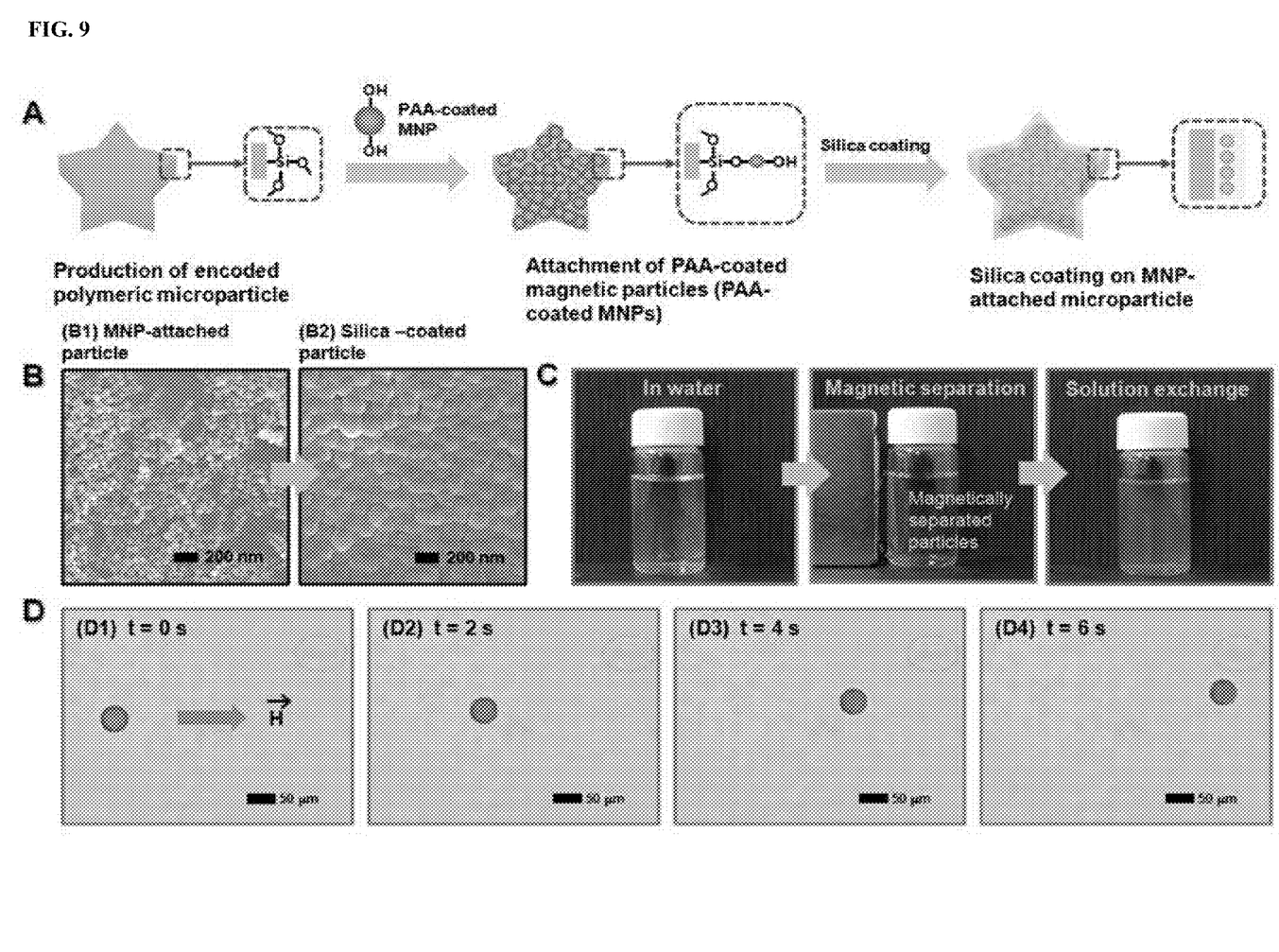
FIG. 9 shows fabrication and manipulation of silica-coated encoded "magnetic" microparticles.

When magnetic materials are incorporated into the microparticles, the use of a magnetic field enables easy separation of desired contents from a carrier solution. FIG. 9 shows fabrication and manipulation of the silica-coated encoded "magnetic" microparticles. FIG. 9A shows fabrication steps for the silica-coated magnetic microparticle. FIG. 9B shows field emission scanning electron microscopy (FE-SEM) images of the magnetic microparticles before (B1) and after (B2) silica-coating process. The magnetic microparticles are obtained by attaching poly(acrylic acid) (PAA)-coated $Fe_3O_4$ nanoparticles on the surface of silane-grafted microparticles. For example, the PAA-coated $Fe_3O_4$ nanoparticles may have a size of 80±10 nm.

FIG. 9C shows a solution exchange process via magnetic separation of carriers. By applying an external magnetic field to a solution, a mixture containing silica-coated magnetic particles as well as the biomolecules bound to those silica-coated magnetic particles can be selectively sorted from the solution mixture.

FIG. 9D shows optical microscopy images showing the magnetic manipulation of the magnetic particle. The free-floating magnetic microparticle easily moves in the direction of the applied external magnetic field. Therefore, the magnetic manipulation of the free-floating magnetic microparticles is useful for bioassays involving a solution exchange. Furthermore, the magnetic separation facilitates washing and concentration of the isolated target that has been bound to particles.

As is apparent from the foregoing, in the method according to the embodiment of the present disclosure, a photocurable material is mixed with a linker having a functional group polymerizable with the photocurable material and an alkoxysilyl group to obtain encoded polymeric microparticle cores, and dipping the encoded polymeric microparticle cores in a silica precursor solution to produce millions of encoded polymeric microparticles. According to the method, the silica coating can be carried out in a single step by a simple process. The incorporation of magnetic nanoparticles into the polymeric microparticles facilitates the manipulation of the particles for bioassays. The presence of silica shells in the encoded microparticles according to the embodiment of the present disclosure ensures good chemical and physical stability and prevents absorption of external biomolecules, enabling accurate analysis. Therefore, the encoded polymeric microparticles can be useful in various applications, including DNA and protein-based diagnostics.

Although the present disclosure has been described in detail with reference to the foregoing embodiments, those skilled in the art will appreciate that various variations and modifications can be made to the embodiments without departing from the spirit and scope of the present disclosure as disclosed in the appended claims.

What is claimed is:

1. Encoded polymeric microparticles, each of which comprises an encoded polymeric microparticle core, a silica shell surrounding the microparticle core, and magnetic materials,
wherein the encoded polymeric microparticle core comprises a photocurable polymer and a linker, and
the encoded polymeric microparticle core is cured by light or electron beam, wherein the photocurable polymer is patterned by optical lithography,
the linker comprises a photocurable functional group chemically bonded with the photocurable polymer and a functional group chemically bonded with the silica shell, and
the linker is a compound represented by the following Formula 1:

[Formula 1]

wherein $R_1$ is hydrogen, methyl or ethyl, each $R_2$ is $C_1$-$C_8$ straight or branched alkyl, and L is $C_1$-$C_{12}$ alkylene, arylene or any combination thereof.

2. The encoded polymeric microparticles according to claim 1, wherein the magnetic materials are placed inside the microparticle core.

3. The encoded polymeric microparticles according to claim 1, wherein the magnetic materials form a layer of magnetic nanoparticles interposed between the microparticle core and the silica shell.

4. The encoded polymeric microparticles according to claim 1, wherein the encoded polymeric microparticle core is connected to the silica shell via —Si—O—Si— bonds.

5. The encoded polymeric microparticles according to claim 1, wherein carboxyl or amine groups are introduced on the surface of the silica shell.

6. The encoded polymeric microparticles according to claim 1, wherein a biomaterial selected from the group consisting of antigens, antibodies, DNAs, RNAs, and oligonucleotides is introduced on the surface of the silica shell.

7. The encoded polymeric microparticles according to claim 1, wherein the encoded polymeric microparticle core is encoded by color or shape.

8. The encoded polymeric microparticles according to claim 1, wherein the size of the encoded polymeric microparticle core is larger than several micrometers.

* * * * *